United States Patent
Bardsley et al.

(10) Patent No.: US 10,314,593 B2
(45) Date of Patent: Jun. 11, 2019

(54) OCCLUSIVE DEVICES

(71) Applicant: Covidien LP, Mansfield, MA (US)

(72) Inventors: Earl Bardsley, San Clemente, CA (US); Richard Rhee, Anaheim Hills, CA (US)

(73) Assignee: Covidien LP, Mansfield, MA (US)

( * ) Notice: Subject to any disclaimer, the term of this patent is extended or adjusted under 35 U.S.C. 154(b) by 741 days.

(21) Appl. No.: 14/862,479

(22) Filed: Sep. 23, 2015

(65) Prior Publication Data

US 2017/0079661 A1    Mar. 23, 2017

(51) Int. Cl.
*A61B 17/12*    (2006.01)
*A61B 17/00*    (2006.01)

(52) U.S. Cl.
CPC .. *A61B 17/12113* (2013.01); *A61B 17/12031* (2013.01); *A61B 17/12172* (2013.01); *A61B 17/12186* (2013.01); *A61B 17/12177* (2013.01); *A61B 2017/00526* (2013.01); *A61B 2017/00893* (2013.01)

(58) Field of Classification Search
CPC . A61F 2/02; A61B 17/1215; A61B 17/12145; A61B 17/12031
See application file for complete search history.

(56) References Cited

U.S. PATENT DOCUMENTS

| | | | |
|---|---|---|---|
| 4,954,126 A | 9/1990 | Wallsten | |
| 5,951,599 A | 9/1999 | McCrory | |
| 6,264,671 B1 | 7/2001 | Stack et al. | |
| 6,497,711 B1 | 12/2002 | Plaia et al. | |
| 6,613,078 B1 | 9/2003 | Barone | |
| 6,652,574 B1 | 11/2003 | Jayaraman | |
| 6,702,843 B1 | 3/2004 | Brown et al. | |
| 7,235,096 B1 | 6/2007 | Van Tassel et al. | |
| RE40,816 E | 6/2009 | Taylor et al. | |
| 8,267,986 B2 | 9/2012 | Berez et al. | |
| 8,409,267 B2 | 4/2013 | Berez et al. | |
| 9,050,206 B2 | 6/2015 | Berez et al. | |
| 2002/0138133 A1 | 9/2002 | Lenz et al. | |
| 2003/0135258 A1 | 7/2003 | Andreas et al. | |

(Continued)

FOREIGN PATENT DOCUMENTS

| | | |
|---|---|---|
| JP | 2011518023 A | 6/2011 |
| JP | 2013509972 A | 3/2013 |

(Continued)

OTHER PUBLICATIONS

European Search Report dated Feb. 2, 2017; European Patent Application No. 16184758.7; 11 pages.

(Continued)

*Primary Examiner* — Julie A Szpira
(74) *Attorney, Agent, or Firm* — Fortem IP LLP; Vijay Kumar

(57) ABSTRACT

An implant can include a single- or dual-layer braided body having a variable porosity. In a dual-layer body, first and second longitudinal sections, having respective first and second porosities, can be overlapped such that the first and second porosities overlap each other. The dual-layer construction can cumulatively provide a third porosity at a distal portion and a fourth porosity at a proximal portion. The third and fourth porosities can each be greater than each of the first and second porosities.

10 Claims, 4 Drawing Sheets

(56) References Cited

U.S. PATENT DOCUMENTS

| | | |
|---|---|---|
| 2004/0133223 A1 | 7/2004 | Weber |
| 2004/0186368 A1 | 9/2004 | Ramzipoor et al. |
| 2006/0064151 A1 | 3/2006 | Guterman et al. |
| 2006/0116713 A1 | 6/2006 | Sepetka et al. |
| 2006/0184238 A1 | 8/2006 | Kaufmann et al. |
| 2006/0206201 A1 | 9/2006 | Garcia et al. |
| 2006/0271153 A1 | 11/2006 | Garcia et al. |
| 2007/0021816 A1 | 1/2007 | Rudin |
| 2007/0055365 A1 | 3/2007 | Greenberg et al. |
| 2007/0239261 A1 | 10/2007 | Bose et al. |
| 2010/0076317 A1 | 3/2010 | Babic et al. |
| 2011/0040372 A1 | 2/2011 | Hansen et al. |
| 2012/0316598 A1 | 12/2012 | Becking |
| 2013/0204351 A1* | 8/2013 | Cox .................. A61F 2/07 623/1.21 |
| 2013/0211495 A1 | 8/2013 | Halden et al. |
| 2014/0094896 A1 | 4/2014 | Berez et al. |
| 2014/0135810 A1 | 5/2014 | Divino |
| 2015/0238333 A1 | 8/2015 | Berez et al. |

FOREIGN PATENT DOCUMENTS

| | | |
|---|---|---|
| WO | 2009132045 A2 | 10/2009 |
| WO | 2013103888 A1 | 7/2013 |
| WO | WO2014085590 | 6/2014 |
| WO | 2014144980 A1 | 9/2014 |

OTHER PUBLICATIONS

Vanninen, et al., "Broad Based Intracranial Aneurysms: Thrombosis Induced by Stent Placement", Am J Neuroradiol, 24: 263-6 (2003).

\* cited by examiner

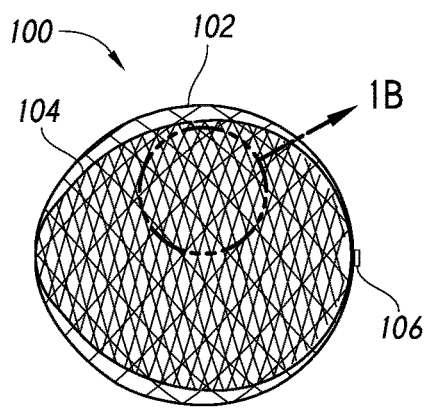
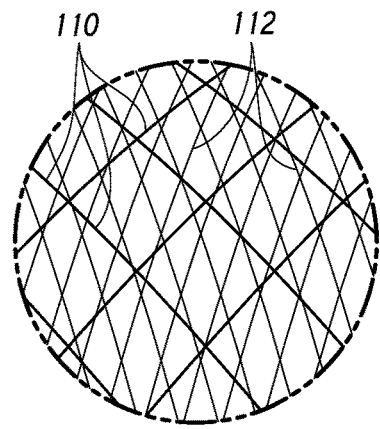
FIG. 1A    FIG. 1B
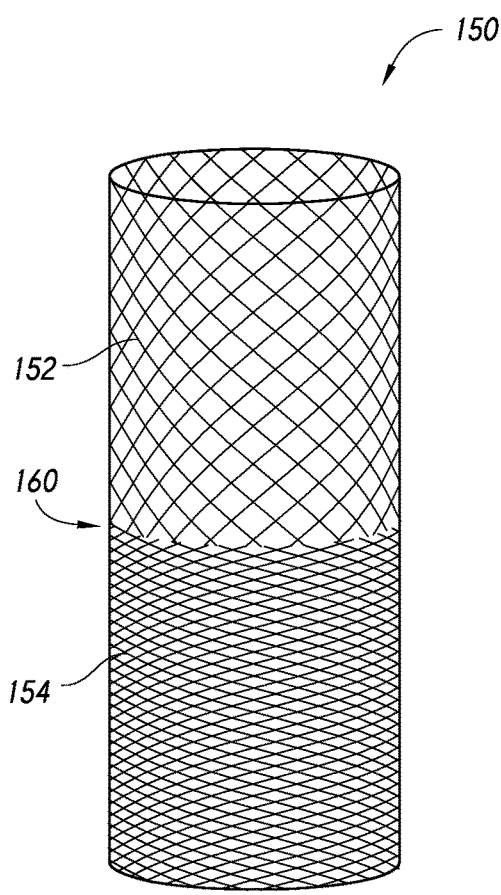
FIG. 2

OCCLUSIVE DEVICES

BACKGROUND

Field of the Inventions

The present technology generally relates to intrasaccular medical devices, and more particularly, to devices formed by layering one or more materials to create a composite porosity for occluding a target area of a patient's vasculature.

Description of the Related Art

Walls of the vasculature, particularly arterial walls, may develop areas of pathological dilatation called aneurysms. As is well known, aneurysms have thin, weak walls that are prone to rupturing. Aneurysms can be the result of the vessel wall being weakened by disease, injury or a congenital abnormality. Aneurysms could be found in different parts of the body with the most common being abdominal aortic aneurysms (AAA) and brain or cerebral aneurysms. When the weakened wall of an aneurysm ruptures, it can result in death.

Aneurysms are generally treated by excluding the weakened part of the vessel from the arterial circulation. For treating a cerebral aneurysm, such reinforcement is done in many ways including: (i) surgical clipping, where a metal clip is secured around the base of the aneurysm; (ii) packing the aneurysm with small, flexible wire coils (micro-coils) or braided ball devices; (iii) using embolic materials to "fill" or "pack" an aneurysm; (iv) using detachable balloons or coils to occlude the parent vessel that supplies the aneurysm; and (v) intravascular stenting.

SUMMARY

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

Systems and procedures for treating aneurysms can include an intrasaccular device having one or more expandable components that can be inserted into an aneurysm to facilitate a thrombotic, healing effect. The components can have specific characteristics, including porosity, composition, material, shape, size, interconnectedness, inter-engagement, coating, etc. These characteristics can be selected in order to achieve a desired treatment or placement of the intrasaccular device.

In accordance with some embodiments, implants or implantable devices and methods of making and using such devices are provided herein. The implantable device can be formed using a braided material, such as a braided tubular component, in accordance with some embodiments.

The implantable device can comprise a single-layer or dual-layer body formed using one or more components that are positioned in a layered relationship relative to each other, thereby overlapping to define at least a portion of the implantable device. For example, in some embodiments, a tubular braided material can be everted onto or inverted into itself such that the tubular braid imparts or provides porosity characteristics to the implantable device based on the porosity characteristics of the tubular component. In particular, some embodiments relate to the use of a tubular component having a variable porosity, such as having two or more sections that each have different porosities such that when positioned in an overlapping relationship, the collective porosity of the overlapping layers provides a composite or collective porosity to the implantable device at a given location on the surface of the implantable device.

In some embodiments, the implantable device can comprise first and second overlapping longitudinal sections that form The filaments 306 can be coupled together at an end using a suture, hub, or marker band 316, such as through the method disclosed in FIGS. 9A-9D. The first and second sections can comprise respective first and second porosities. In some embodiments, the first and second sections can be coupled to each other at a fold wherefrom the first and second sections extend. The second section can be in an everted or inverted position to overlap the first section. The first and second porosities can be aggregated or combined to provide a third porosity. For example, the device can define a third porosity at a distal portion of the device and a fourth porosity at a proximal portion of the device. In some embodiments, the third and fourth porosities can be greater than the first and second porosities.

The first and second porosities of the first and second sections can be substantially constant along the first and second sections. However, the first porosity can increase and/or decrease along the length of the first section, one or more times. Similarly, the second porosity can increase and/or decrease, one or more times, along the length of the second section. Through the use of such innovative patterns and manufacturing techniques, the implantable device can be configured to define any of a variety of unique porosity profiles, such as those disclosed and illustrated herein.

The subject technology is illustrated, for example, according to various aspects described below. Various examples of aspects of the subject technology are described as numbered embodiments (1, 2, 3, etc.) for convenience. These are provided as examples and do not limit the subject technology. It is noted that any of the dependent embodiments may be combined in any combination with each other or one or more other independent embodiments, to form an independent embodiment. The other embodiments can be presented in a similar manner. The following is a non-limiting summary of some embodiments presented herein:

Clause 1. An implant for occluding an aneurysm, comprising: a dual-layer braided body having distal and proximal portions and first and second longitudinal sections, the first and second sections having respective first and second porosities, the second section being everted to overlap the first section such that the distal portion comprises a fold, the first and second porosities overlapping each other to provide a third porosity at the distal portion and a fourth porosity at the proximal portion, the fourth porosity being greater than the third porosity.

Clause 2. The implant of Clause 1, wherein the fourth porosity is less than the second porosity.

Clause 3. The implant of any of the previous Clauses, wherein the fourth porosity is constant from the proximal portion across a midsection of the body.

Clause 4. The implant of any of the previous Clauses, wherein the fourth porosity is less than the first porosity.

Clause 5. The implant of any of the previous Clauses, wherein the second porosity is less than the first porosity.

Clause 6. The implant of any of the previous Clauses, wherein the first and second porosities are different from each other.

Clause 7. The implant of any of the previous Clauses, wherein the first porosity is substantially constant along the first section.

Clause 8. The implant of any of the previous Clauses, wherein the first porosity increases in a direction away from the second section.

Clause 9. The implant of any of the previous Clauses, wherein the second porosity is substantially constant along the second section.

Clause 10. The implant of any of the previous Clauses, wherein the second porosity decreases in a direction away from the first section.

Clause 11. The implant of any of the previous Clauses, wherein the body comprises a cross-sectional profile that is substantially cylindrical from a midsection of the body to the proximal portion, the body tapering such that the first and second sections converge toward each other at the proximal portion.

Clause 12. The implant of Clause 11, wherein the proximal portion is substantially flat.

Clause 13. A method of making an embolic device, the method comprising: positioning a tubular braid over a wire, the tubular braid having first and second longitudinal sections being longitudinally positioned on opposite sides of a midsection of the tubular braid, the first and second sections having respective first and second porosities; constraining the midsection in a substantially closed configuration on the wire; inverting the first section over the second section to produce a dual-layer tubular section having a closed end at the midsection and an open end opposite the closed end; inserting a form within the dual-layer section through the open end such that the form is positioned axially between the closed end and the open end; and setting a device body shape based on the form.

Clause 14. The method of Clause 13, further comprising after setting the device body shape, removing the form in one piece from the braid.

Clause 15. The method of any of Clauses 13-14, wherein the first porosity is different than the second porosity.

Clause 16. The method of any of Clauses 13-15, wherein the first porosity is substantially constant along the first section.

Clause 17. The method of any of Clauses 13-16, wherein the first porosity increases in a direction away from the second section.

Clause 18. The method of any of Clauses 13-17, wherein the second porosity is substantially constant along the second section.

Clause 19. The method of any of Clauses 13-18, wherein the second porosity decreases in a direction away from the first section.

Clause 20. The method of any of Clauses 13-19, wherein the setting comprises setting a cross-sectional profile that is substantially cylindrical from the midsection of the body to the second section, the body tapering such that the first and second sections converge toward each other at the second end.

Clause 21. An implant having any of the features of any of the previous Clauses.

Clause 22. A method of manufacturing any of the implants or assemblies of any of the previous Clauses.

Clause 23. An implant for occluding an aneurysm, comprising: a braided body comprising a plurality of braided filaments, the braided body having distal and proximal portions along a longitudinal axis of the body, first and second longitudinal sections, and a transition section between the first and second longitudinal sections, the first and second longitudinal sections having respective first and second porosities, the transition section having a third porosity that changes from the first porosity to the second porosity, wherein a pitch of braided filaments changes along the length of the longitudinal axis to define first, second, and third porosities.

Clause 24. The implant of Clause 23, wherein the first and second porosities are substantially constant along the first and second longitudinal sections.

Clause 25. The implant of any of Clauses 23-24, further comprising a third longitudinal section and a second transition section, wherein the second longitudinal section is interposed between the first longitudinal section and the third longitudinal section, and wherein the second transition section is interposed between the second longitudinal section and the third longitudinal section, wherein the third longitudinal section comprises a fourth porosity, different from the second porosity, and wherein the second transition section comprises a fifth porosity that changes along the longitudinal length of the second transition section.

Clause 26. The implant of Clause 25, wherein the fourth porosity is substantially equal to the first porosity.

Clause 27. The implant of any of Clauses 25-26, wherein the first porosity and the fourth porosity are greater than the second porosity.

Clause 28. The implant of any of Clauses 25-26, wherein the first porosity and the fourth porosity are less than the second porosity.

Clause 29. The implant of any of Clauses 23-28, wherein the body comprises a cross-sectional profile that is substantially cylindrical from a longitudinal midsection of the body to the distal and proximal portions, the body thereafter tapering along the longitudinal axis such that the distal and proximal portions converge toward the longitudinal axis.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

FIG. 1A illustrates an embodiment of a dual-layer braided implant for occluding an aneurysm, according to some embodiments.

FIG. 1B is an enlarged partial view of the dual-layer implant of FIG. 1A.

FIGS. 2-4 illustrate tubular components for manufacture of a dual-layer braided implant, according to some embodiments.

DETAILED DESCRIPTION

Figure 3:
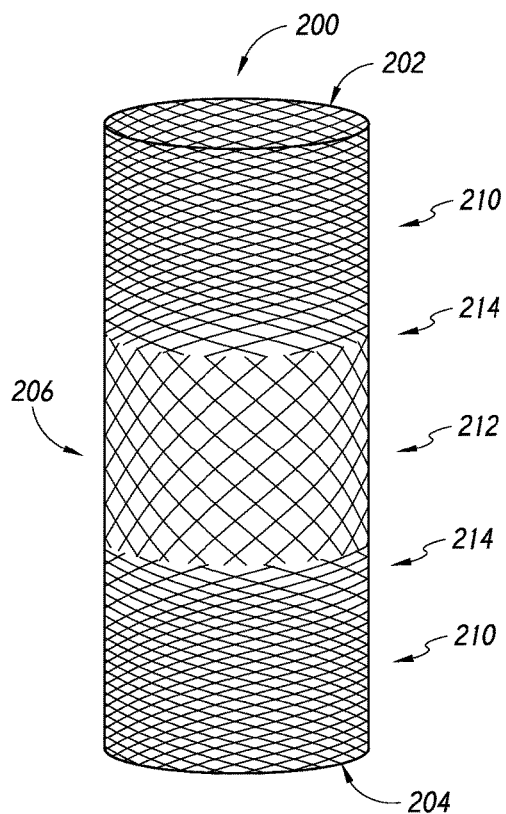

In the following detailed description, numerous specific details are set forth to provide a full understanding of the subject technology. It should be understood that the subject technology may be practiced without some of these specific details. In other instances, well-structures and techniques have not been shown in detail so as not to obscure the subject technology.

In accordance with some embodiments, an implantable device can be provided that comprises a variable porosity, having two or more sections that enable the device to selectively restrict flow through or into an aspect of the vasculature. The implant can comprise a desired shape, such as a barrel, cylindrical, oval, or spherical, or any combination thereof. Further, the implant can comprise a single layer construction or a dual-layer construction. Although some embodiments illustrated in the accompanying figures demonstrate a dual-layer construction, the principles and teachings provided herein can be applied to single-layer constructions as well.

Referring now to FIG. 1A, an implantable device 100 can be provided that comprises a first layer 102 and a second layer 104. The first layer 102 can be an outer layer that extends around an entirety of an outer surface of the device 100. The first and second layers 102, 104 can be coupled together at one or both ends using a suture, hub, or marker band 106, such as through the method disclosed in FIGS. 5A-5D. However, in some embodiments, the outer layer 102 can extend around less than the entire outer surface of the device 100, such as covering at least 90% of the outer surface, at least 80% of the outer surface, at least 70% of the outer surface, or at least 60% of the outer surface. Additionally, the inner layer 104 can extend within the outer layer 102 and cover or extend about substantially all of the inner surface area of the implantable device 100. However, the inner layer 104 can extend along less than the entire inner surface of the device 100, such as at least 90%, at least 80%, at least 70%, or at least 60% of the implantable device 100.

As it used herein, the term "porosity" can refer to the surface porosity of the implantable device. The surface porosity can be defined as the ratio of empty space (i.e., the surface area of the openings in the mesh material and/or frame) and the total surface area of the given region of the device. In order to calculate the porosity of the implantable device along a specific region of the frame covered by mesh material, the surface area of the openings may be found by first determining the total surface area of filaments in the specific region, accounting for all filaments in the specific region, and calculating a topographical or 2-D representation of total filament area, based on the dimensions (width or diameter and length) of filaments of the frame and/or the dimensions (width or diameter and length) of filaments of the mesh material. The total surface area of the frame and/or mesh material can then be subtracted from the total surface area of the given region in order to provide a resulting surface area of the openings or openings in the given region.

In calculating the porosity of a given region or section of the device, a person of skill in the art can use images of a given device to guide or facilitate the calculation of the opening surface area and total surface area ratio. Such a calculation can rely on known information regarding the size and/or quantity of fibers or filaments in the frame and/or mesh material used in the implantable device.

Additionally, some embodiments may refer to high or low porosity or filament pitch, which can be a surrogate for porosity. Additionally, a "pic count," which is the number of filament crossings per unit length, can also be used as a measure of the ability of a device to promote or restrict flow through a composite surface or layers. In some embodiments, different regions of the implantable device can have pic counts that vary relative to each other.

When the implantable device 100 is viewed in an enlarged view, such as that illustrated in FIG. 1B, the outer layer 102 can more readily be illustrated as a plurality of filaments 110 that overlap a plurality of filaments 112 of the inner layer 104. As illustrated in FIG. 1B, the filaments 110 can collectively define a first porosity. Similarly, the filaments 112 can collectively define a second porosity. The first and second porosities can collectively create a cumulative, composite, or combined porosity for the implantable device 100 at a given location of the implantable device 100. Because the first and second porosities can vary along the inner and outer layers 102, 104, the corresponding composite porosity of the device 100 at the given location can also change relative to another location along the device.

For example, in accordance with some embodiments, a single tubular member can be used to form the implantable device 100. Although not exhaustive, examples of tubular members having different porosities are shown in FIGS. 2-4.

Referring to FIG. 2, a tubular member 150 is illustrated in which the tubular member 150 comprises a first section 152 and a second section 154 that are formed such that the first and second sections 152, 154 define different porosities. The first and second sections 152, 154 can be joined together at a midsection or transition section 160, which can lie at a longitudinal midpoint of the tubular member 150. The first and second sections 152, 154 can meet at the transition section 160 as a pitch of the braid pattern changes, thereby creating a change in the porosity of the tubular member 150.

Figure 4:
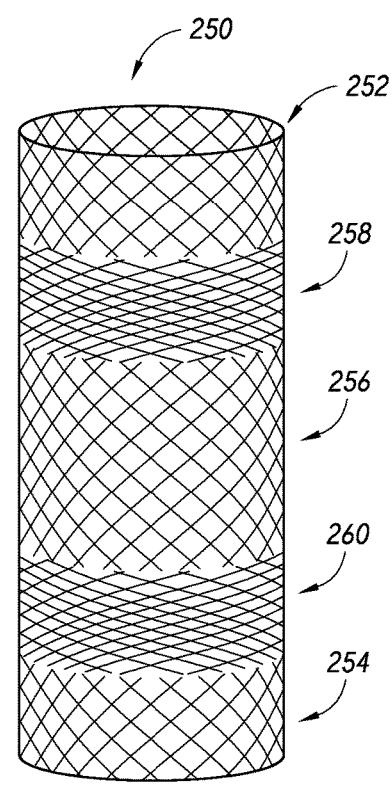

FIG. 3 illustrates another embodiment of a tubular member 200 that comprises first and second end sections 202, 204 and a central portion 206 positioned therebetween. The pitch of the braid pattern can change along the longitudinal extent of the tubular member 200. For example, as illustrated, at the first end section 202 of the tubular member 200, the pitch of the braid pattern can be relatively low compared to the pitch of the braid pattern in the central section 206 of the tubular member 200. However, as the braid pattern continues toward the second end section 204, the pitch can become relatively higher compared to the central section 206. Therefore, the central section 206 can provide a braid pattern that has higher porosity than the braid pattern in the tubular member 200 adjacent to the first and second end sections 202, 204.

In some embodiments, the tubular member 200 can comprise one or more low porosity sections 210 and one or more high porosity sections 212, as well as transition sections 214 disposed between the low porosity sections 210 and the high porosity sections 212. The porosity can vary between these sections, for example, as the pitch of the braid pattern changes. Additionally, the change in pitch and/or porosity can also be quantified as a change in pic count.

For example, the low porosity section 210 and the high porosity section 212 of the implantable device can have a pic count ratio of about 1.2:1, 1.5:1, 1.7:1, 1.8:1, 2:1, 2.3:1, 2.5:1, 2.7:1, 2.9:1, 3:1, 3.2:1, 3.3:1, 3.5:1, 3.7:1, 3.9:1, 4:1, 4.2:1, 4.3:1, 4.5:1, 4.7:1, 4.9:1, 5:1, 5.2:1, 5.3:1, 5.5:1, 5.7:1, 5.9:1, 6:1, 7:1, 8:1, 9:1, or 10:1, or any number within this range of numbers. For example, the low porosity section 210 can have a pic count of between about 80 to about 150 pics per square inch, between about 90 to about 120 pics per square inch, or between about 100 to about 110 pics per square inch. Further, the high porosity section 212 can have a pic count of between about 20 to about 80 pics per square inch, between about 30 to about 60 pics per square inch, or between about 40 to about 50 pics per square inch.

Furthermore, low and high porosity sections 210, 212 can be separated by the transition section 214 in which the pic count changes from a high pic count in the low porosity region to a lower pic count in the high porosity region. The transition section 214 can have a longitudinal length (measured along an axis of the tubular member 200) of less than half, less than one-third, or less than one-fourth of the length of the low porosity section 210 or the high porosity section 212. Accordingly, in any of the embodiments disclosed herein, a braid pattern can change gradually or abruptly when transitioning from a low pitch to a high pitch and vice versa.

Referring now to FIG. 4, yet another tubular member 250 is illustrated. The tubular member 250 can comprise a first end section 252, a second end section 254, a central portion 256, a first intermediate section 258, and a second intermediate section 260. Similar to the discussion above with respect to FIG. 3, the pitch of the braid pattern can vary along the tubular member 250 from the first end section 252 and along the first intermediate section 258, the midsection 256, and the second intermediate section 260 until reaching the second end section 254. Thus, as illustrated, the first and second intermediate sections 258, 260 can comprise a braid pattern having a lower pitch, thereby providing a higher density pattern that has a low porosity relative to the braid pattern adjacent to the first end section 252, the midsection 256, and the second end section 254.

Various other embodiments can be provided by reversing the patterns illustrated in FIGS. 2-4 of the pitch of the braid pattern and/or by adding or removing sections of the tubular braid in which the pitch of the thread pattern changes. Accordingly, although the embodiments illustrated in FIGS. 2-4 illustrate tubular members having two, three, or five different pitch or porosity patterns two, three, or five different sections along which the pitch or porosity of the braid pattern changes, the tubular member can comprise four, six, seven, eight, or more different sections along which the pitch or porosity of the braid pattern changes.

Further, although in some embodiments, the pitch or porosity can vary between a "high" porosity value and a "low" porosity value (i.e., between two porosity values), the braid pattern can vary such that the tubular member comprises a variety of different porosity values or pitch values such that one or more sections of the tubular member comprises a unique pitch value or porosity value. For example, the pitch value or porosity value can be determined by calculating an average pitch or an average porosity across the given section.

Additionally, the length of a section can be determined by identifying the locations of all of the high or low pitch or porosity values (which points represent a "center point" of a given section) and identifying the distance from the center point, to the left and right, of "midpoints" between adjacent center points. The midpoints represent the location at which the pitch or porosity is at an average between the adjacent center points. Such measures can be used to determine longitudinal lengths of respective sections of a tubular member, if necessary, according to some embodiments disclosed herein.

Moreover, although FIGS. 3 and 4 illustrate embodiments of tubular members having one or more low porosity sections, one or more high porosity sections, and corresponding transition sections, other various combinations can be provided. Further, when multiple low porosity sections are used, the porosity, pic count, or braid pitch of a given low porosity section can be substantially equal to that of another low porosity section or different from that of another low porosity section. Similarly, when multiple high porosity sections are used, the porosity, pic count, or braid pitch of a given high porosity section can be substantially equal to that of another high porosity section or different from that of another high porosity section. Furthermore, three, four, five, six, seven, eight, nine, or more different sections (whether high porosity, low porosity, or transition sections) can be used in some embodiments. For example, a tubular member can comprise, starting from a first end: a low porosity section, a transition section, a high porosity section, a transition section, a lowest porosity section, a transition section, a highest porosity section, a transition zone, a lowest porosity section, a transition section, a high porosity section, the transition zone, and a low porosity section. Any of a variety of combinations and configurations can be prepared in order to achieve desired mechanical and/or flow characteristics for the implant.

Figure 5A:
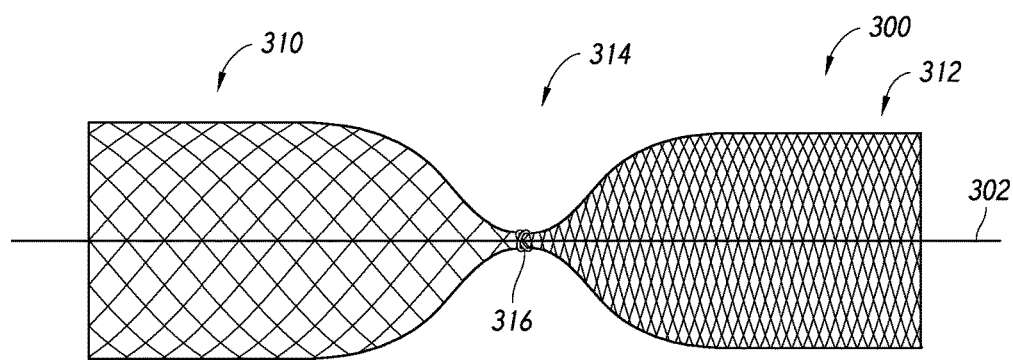
FIGS. 5A-5D illustrate aspects of a method of making an embolic device, according to some embodiments.
Figure 5B:
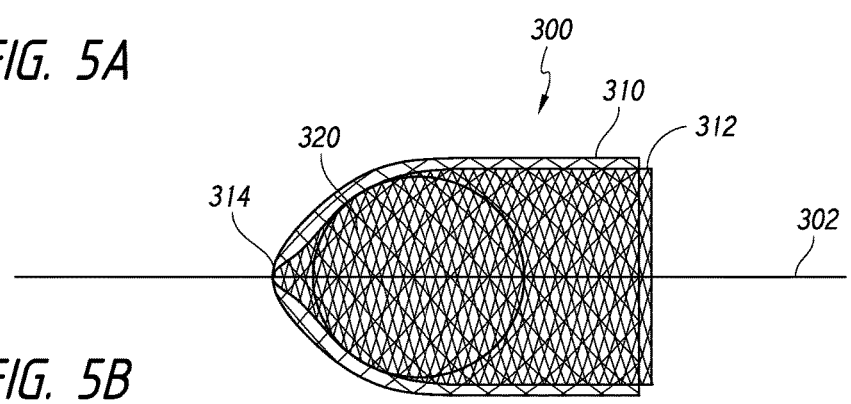
Figure 5C:
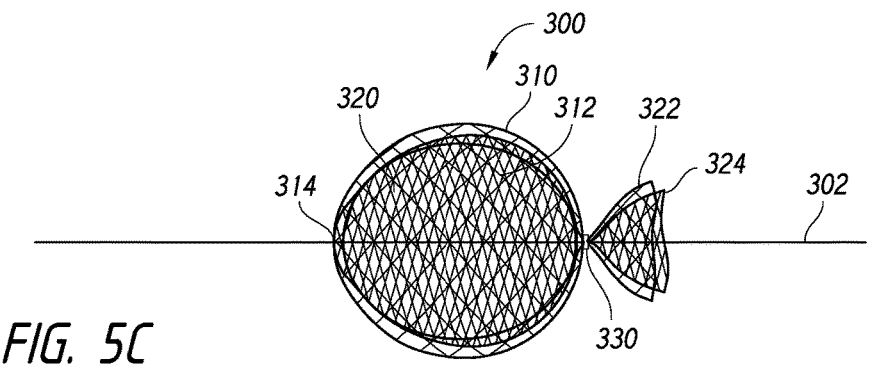

Referring now to FIGS. 5A-5D, a method for manufacturing a dual-layer implantable device will now be discussed. FIG. 5A illustrates placement of a tubular member 300 over a wire 302. The tubular member comprises a first end section 310 and a second end section 312. The tubular member 300 also defines a midsection 314 that can be collapsed or drawn towards the wire 302 by placing a suture or tie 316 onto the tubular member 300. After the midsection 314 has been constrained or tied to the wire 302, resulting in a substantially closed midsection 314, a form or insert 320 can be inserted into a lumen of the tubular member 300. Thereafter, as illustrated in FIG. 5B, the first end section 310 can be inverted over the midsection 314 and the second end section 312 such that the tubular member 300 assumes a dual-layer configuration.

Thereafter, as illustrated in Figured 5C, the ends 322, 324 of the first and second end sections 310, 312 can be collapsed towards the wire 302 in order to stretch the first and second sections around the form 320. The ends 322, 324 can be secured in the collapsed state onto the wire 302. This aspect of the method can be done using another suture, hub, or marker band, as shown by element 330, or by using a form or other equipment to compress the first and second sections around the insert 320. When in position, the device shape can be set by application of heat (e.g., Nitinol can be shape set at 550° C. for five minutes). Other features and aspects of such methods can be implemented in accordance with the disclosure found in U.S. patent application Ser. No. 13/048,648, filed on Mar. 15, 2011, the entirety of which is incorporated herein by reference.

Figure 5D:
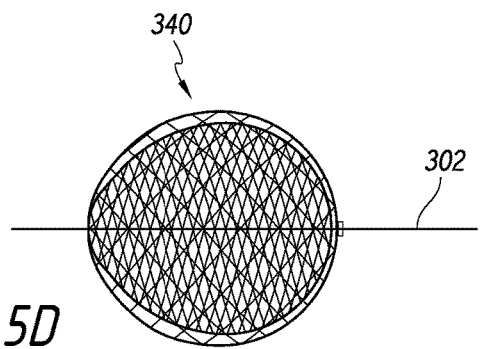

After the device shape is set, a completed implantable device 340 can be formed by removing the tail or ends 322, 324, as shown in FIG. 5D.

In addition, methods for manufacturing a single-layer implantable device can also be provided in which, in contrast to the method described with respect to FIGS. 5A-5D, after the tubular member is placed over a wire, and a form or insert is inserted into a lumen of the tubular member, opposing ends of the tubular member can be collapsed towards the wire in order to stretch the tubular member over the form. The ends of the tubular form can be secured in the collapsed state onto the wire using a suture, hub, or marker band. Thereafter, any excess material (i.e., tails) from the tubular member can be trimmed and the single-layer braid body can be finalized by removing it from the wire. The form can be removed, such as disclosed in U.S. patent application Ser. No. 13/048,648, filed on Mar. 15, 2011, the entirety of which is incorporated herein by reference.

FIGS. 6-9 illustrate various embodiments of implantable devices formed using the methods and components disclosed herein. In accordance with some embodiments, these figures can illustrate schematically the porosity of a single-layer braided body of the implantable device or, for dual-layer braided bodies, a resultant, composite, or cumulative porosity of the implantable device based on the underlying porosities of inner and outer layers.

Figure 6:
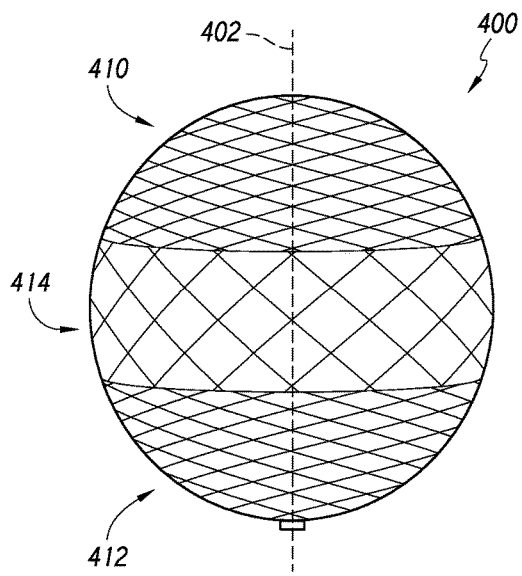
FIGS. 6-9 illustrate embodiments of dual-layer braided implants, according to some embodiments.

For example, by inverting the tubular member 150 illustrated in FIG. 2, an implantable device 400 may be formed, as illustrated in FIG. 6. In such an embodiment, the collapsing of the tubular member toward a longitudinal axis 402 of the device 400 at a distal portion 410 and at a proximal portion 412 will cause the filaments of the braid to converge more closely towards each other at the distal and proximal portions 410, 412, thereby resulting in a relatively lower pitch, higher density, or lower porosity in the distal and proximal portions 410, 412 relative to a central section 414 of the implantable device 400.

Figure 7:
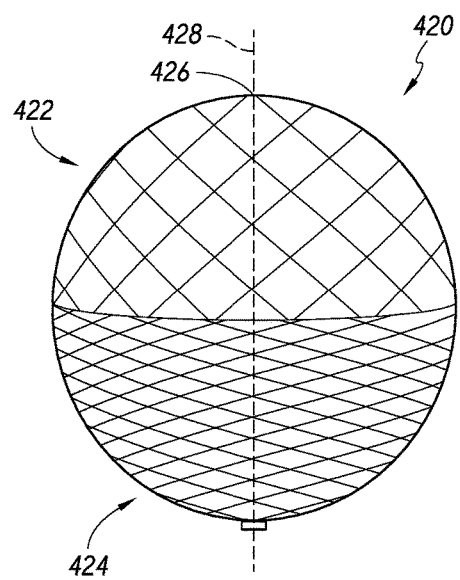

Referring now to FIG. 7, another implant 420 is shown in which a composite porosity or pitch of the braid pattern results in a profile in which a distal portion 422 has a relatively higher porosity and higher pitch than a proximal portion of the device 420. The implant 420, formed using the tubular member 200, such as that illustrated such as the tubular member 200 shown in FIG. 3, can achieve the variation in porosity and pitch given that the eversion or transition between the implant outer layer to the implant inner layer would occur at position 426, which corresponds to the midpoint or central section 206 of the tubular member 200 that is collapsed toward the longitudinal axis 428. Therefore, the distal portion 422 of the implant 420 represent the doubled-over layering of the midsection 206 of the tubular member 200, which maintains a relatively higher cumulative porosity that the layering of the already relatively lower porosity first and second end sections 202, 204. Indeed, the overlap of the relatively lower porosity first and second end sections 202, 204 in the proximal portion 424 of the implantable device 420 causes the cumulative porosity in the proximal portion 424 to be much less than that of the distal portion 422.

Figure 8:
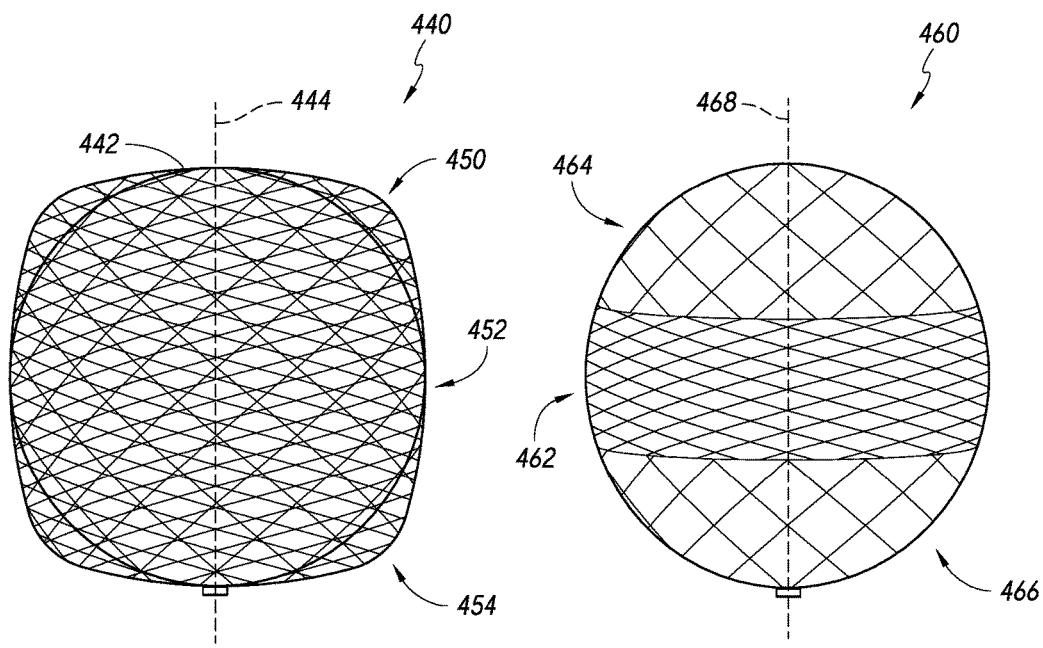
Figure 9:
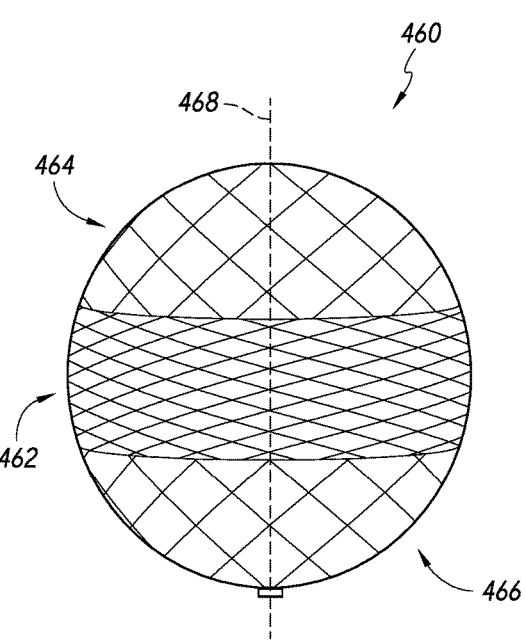

Referring now to FIGS. 8 and 9, alternative embodiments of implantable devices are illustrated as relating to the product created using the tubular member 250 shown in FIG. 4. The variation achieved from the implantable device 440 of FIG. 8 and the implantable device 460 shown in FIG. 9 is made possible depending on the magnitude difference in the high and low porosities or pitch is of the braid pattern of the tubular member 250, which will be explained further below.

FIG. 8 illustrates the product of everting the tubular member 250 in a manner described in the process shown in FIGS. 5A-5D. The midsection 256 of the tubular member 250 corresponds to location 442, shown in FIG. 8. The overlapping portions of the midsection 256 thus form the distal portion 450 of the device 440. Thus, the tubular braid will be collapsed toward a longitudinal axis 444 of the device 440, thereby causing filaments of the midsection 256 to converge towards each other, increasing the pitch and decreasing the porosity of the midsection 256. This collapsing of the midsection 256 (of a high porosity section) can result in a porosity that can be similar and/or substantially equal to the composite porosity of the first and second intermediate sections 258, 260 when overlapping each other.

Further, the first and second end sections 252, 254, which have a relatively higher porosity than the adjacent first and second intermediate sections 258, 260, will also changed when be combined to provide a collapsed, composite porosity that is much lower and more similar to that of the first and second intermediate sections 258, 260 in the central section 452 of the device 440. Thus, the proximal portion 454 of the device 440 can define a porosity or pitch that is similar to or substantially equal to the porosity or pitch of the central section 452, which in turn is similar to or substantially equal to the porosity or pitch of the distal portion 450.

Accordingly, FIG. 8 demonstrates that a braided device can be formed that has respective proximal and distal portions that converge toward a longitudinal axis of the device, resulting in lower porosity, but nevertheless, the device defines a composite porosity that is substantially constant along the entirety of the outer surface of the device.

Further, if modified, the tubular member 250 can be configured such that the first and second intermediate sections 258, 260 define a pitch that is substantially less than the pitch in the first end section, second end section, and midsection, 252, 254, 256. In such a situation, the embodiment of the device 460 shown in FIG. 9 can be achieved.

As similarly described with respect to FIG. 8, the formation of the device 460 can result in a central section 462 that has a much lower porosity (i.e., a much lower pitch) than in the corresponding distal or proximal portions 464, 466. As noted above, this result can be achieved by virtue of a significant increase in the pitch between the sections such that the first and second intermediate sections 258, 260 define a much lower pitch than the first end section, second end section, or midsection 252, 254, 256 of the tubular member 250. Thus, when collapsed about a longitudinal axis 468 of the device 460, the central section 462 can provide relatively lower porosity compared to the distal and proximal portions 464, 466.

In some embodiments, a composite structure of the implantable device can comprise three materials having different porosities. Further, the composite structure of the implantable device can comprise for, five, six, or more different materials having different porosities. Some embodiments of the implantable device can be configured to provide a specific porosity profile. The porosity profile can comprise a single, consistent average porosity across the surface of the entire implantable device, or multiple average porosity zones, sections, portions, or regions having different average porosities that collectively form a composite implantable device.

For example, some embodiments can be configured to have a low average surface porosity. For purposes of illustration, high surface porosity is illustrated in the figures using hexagonal patterns with larger-sized hexagons compared to hexagonal patterns with smaller-sized hexagons, which are used to illustrate medium and low porosity structures. Low surface porosity can provide higher resistance to blood flow therethrough, which can facilitate thrombogenesis. When such low porosity implantable devices are implanted into an aneurysm, such devices can tend to isolate the aneurysm from the parent vessel and minimize blood flow velocity within the aneurysm while supporting the aneurysm wall.

Conversely, as surface porosity increases, blood flow through the implantable device can increase, thereby tending to provide less support for thrombogenesis due to lower resistance to flow therethrough. Nevertheless, the realization of some embodiments disclosed herein is that high porosity structures can also support the aneurysm wall, beneficially aid in healing and thrombogenesis for select aneurysm morphologies, permit flow to other vessels (e.g., branch vessels, perforating arteries, or arterioles), and/or permit the introduction of other materials, such as a liquid embolic, etc.

The porosity of the implantable device may vary along any portion(s) or section(s) thereof, including any combination of pore sizes of 1 micron or greater. Further, the pores or openings of the frame and mesh component(s) can range from about 1 µm to about 400 µm, from about 5 µm to about 300 µm, from about 8 µm to about 200 µm, from about 10 µm to about 150 µm, from about 15 µm to about 80 µm, or in some embodiments, from about 20 µm to about 50 µm. Further, at least a portion or section of the device can comprise an average porosity of between about 1 µm and about 150 µm. Further, at least a portion or section can comprise an average pore size of between about 100 µm and about 200 µm. Furthermore, at least a portion or section can comprise an average pore size of between about 200 µm and about 300 µm. When an implantable device is formed using multiple sections or portions, each section or portion can have an average porosity within any of the ranges discussed above. Furthermore, a pore size can be calculated using an "inscribed circle" calculation in which size of a given pore is represented by the diameter of the largest circle that fits into the given pore.

Further Embodiments

In accordance with some embodiments, at least a portion or section of the implantable device can comprise a coating or material for enhancing therapeutic, expansive, or imaging properties or characteristics of at least one or every implantable device.

In some embodiments, the implantable device can be coated with a biocompatible material to promote endothelialization or provide a therapeutic effect.

The coating may include thrombogenic coatings such as fibrin, fibrinogen or the like, anti-thrombogenic coatings such as heparin (and derivatives thereof), urukinase or t-PA, and endothelial promoting coatings or facilitators such as, e.g., VEGF and RGD peptide, and/or combinations thereof. Drug-eluting coatings and a drug-eluting foam composite, such as anti-inflammatory or antibiotic, coatings are also envisioned. These drug-eluting components may include nutrients, antibiotics, anti-inflammatory agents, antiplatelet agents, anesthetic agents such as lidocaine, and anti-proliferative agents, e.g. taxol derivatives such as paclitaxel. Hydrophilic, hygroscopic, and hydrophobic materials/ agents are also envisioned.

Optionally, the implantable device can also comprise an expansion-limiting coating that slows expansion of the device from its natural rate of expansion to a slower rate of expansion such that in the process of expanding, the position of the device can be adjusted within the aneurysm or the device can be removed from the aneurysm, if necessary. Examples of polymers that can be used as expansion-limiting coatings can include hydrophobic polymers, organic non-polar polymers, PTFE, polyethylene, polyphenylene sulfide, oils, and other similar materials.

Further, in accordance with some embodiments, the implantable device or a portion or section of the implantable device can be packed with a liquid embolic during or subsequent to placement of the implantable device. The injection of a liquid embolic can increase the overall packing density within the implantable device.

One suitable liquid embolic is the Onyx™ liquid embolic system manufactured by Covidien LP, Irvine, Calif. Onyx™ liquid embolic system is a non-adhesive liquid used in the treatment of brain arteriovenous malformations. Onyx™ liquid embolic system is comprised of an EVOH (ethylene vinyl alcohol) copolymer dissolved in DMSO (dimethyl sulfoxide), and suspended micronized tantalum powder to provide contrast for visualization under fluoroscopy. Other liquid embolic solutions are also envisioned.

In embodiments, only specific segments of the implantable device may be embedded or coated with an agent to provide desired characteristics to the implantable device(s). For example, an implantable device can comprise a non-thrombogenic coating may be applied to a lower half of the implantable device to minimize clotting at this location. Such coatings may be desirable in aneurysms located at a bifurcation such that blood flow to branch arteries is permitted through the segment of the foam structure having the non-thrombogenic coating. The coated area may be a different color than the remaining portion or section of the implantable device to assist the surgeon in identifying this area.

Optionally, the coated area can also comprise radiopaque material to assist the surgeon in visualization and placement of the implantable device in a desired orientation relative to the aneurysm. The implantable device can have radiopacity characteristics either by adding radiopaque filler to the material (which in some embodiments comprises a foam material), such as bismuth, or attaching radiopaque markers. Alternatively, a radiopaque material can be coupled to the implantable device, such as by dipping, spraying, or otherwise mechanically, chemically, or thermally coupled, injected into, or blended into to the implantable device.

Delivery Methods

Furthermore, delivery systems and procedures can be implemented for delivering an implantable device comprising one or more implantable devices, as discussed herein. Further, a system and method are provided for delivery of an implantable device to an aneurysm and/or recapturing the device for removal or repositioning.

According to some embodiments, one or more of implantable devices can be released into a target aneurysm and, in some embodiments, specifically oriented relative to the aneurysm ostium or neck and/or one or more perforating vessels (e.g., perforating arteries or arterioles) adjacent to the aneurysm.

In use, an access catheter is advanced within the neurovasculature as is conventional in the art. A suitable microcatheter adaptable for navigation through the tortuous neurovascular space to access the treatment site is disclosed in commonly assigned U.S. Pat. No. 7,507,229, the entire contents of which are hereby incorporated herein.

In accordance with some embodiments, when the implantable device comprises a braided material (i.e., when the implantable device is formed using a tubular braid), one of the advantages provided by some embodiments includes the ability to use any of a variety of braid and/or wire configurations. For example, the tubular braid can be formed using as few as 4, 5, or 6 wires. A distinct advantage of some embodiments is a minimal frame with the minimal amount of braid mesh. Another advantage of some embodiments is the substantially reduced profile possible during advancement of the device compared to other devices that use 36, 72, 144, or more wires. Such a reduced profile enables some embodiments to be delivered through much lower-sized catheters, such as 6 Fr, 5 Fr, or 4 Fr. The number of wires can be determined by counting the number of wire ends at the end of the braided tube. In some embodiments having a lower number of wires, e.g., 12 or fewer wires, the primary function of the frame is to provide structural and expansion characteristics. Thus, in such embodiments, the mesh component can primarily provide a desired porosity profile for the implantable device.

In some embodiments, the implantable device can be repositioned within the aneurysm as the device is expanding. The repositioning of the device can allow a clinician to position a lower porosity section of the device adjacent to or away from the neck of the aneurysm. The repositioning of the device can also allow a clinician to position a higher average porosity section of the device adjacent to one or more perforating vessels (e.g., perforating arteries or arterials) adjacent to the aneurysm. The repositioning of the device can also allow a clinician to position a lower porosity portion or section of the device adjacent to a bifurcation. The repositioning of the device can also allow a clinician to position a higher average porosity portion or section of the device toward or in the fundus of the aneurysm. For example, the portions or sections of the device can be positioned at the neck of an aneurysm to significantly reduce blood flow into the weakened structure and promote resultant endothelialization in the aneurysm.

Further, in accordance with some embodiments, the implantable device or a portion of the implantable device can be used in conjunction with other treatment modalities. For example, the implantable device can be delivered and subsequently packed with a liquid embolic The injection of a liquid embolic can increase the overall packing density within the implantable device. Additionally, coils can be introduced through an open end or pore of the implantable device.

The implantable device may provide a support or scaffold for supplemental devices or materials, including coils, expandable components (e.g., foam components), or other materials (e.g., a liquid embolic, drug, radiopaque material, contrast agent, or other agent). The implantable device, framing structure, mesh component, coils, and/or other components thereof may contain or be coated with another material. For example, the coating may be a bioactive coating that promotes specific clinical theory such as endothelialization, thrombosis, etc.

In implementing a method for placing an implantable device within an aneurysm and injecting coils, expandable components, or other materials into the implantable device, the open end or widest interstices of the implantable device can be positioned at the neck of the aneurysm so as to facilitate insertion of the distal end of the catheter into the open end or between the filaments (i.e., into an interstice) of the implantable device. In embodiments having a braided material for the implantable device, the braid pattern can be properly aligned to facilitate entry of the materials into the implantable device. As in other embodiments disclosed herein, the implantable device can comprise a radiopaque material or component that facilitates visualization and enables the clinician to align the implantable device as needed within the aneurysm.

The composite effect of the coils, expandable components, and/or other materials inserted into the implantable device can provide the advantages and benefits discussed above with respect to various other implantable devices. As such, the clinician can determine and control various intrasaccular implant characteristics, including porosity, composition, material, shape, size, interconnectedness, inter-engagement, coating, etc.

According to some embodiments, systems or kits having an implantable device and at least one coil, expandable component, and/or other material can be provided.

Further Aspects of Some Embodiments

The apparatus and methods discussed herein are not limited to the deployment and use of a medical device or stent within the vascular system but may include any number of further treatment applications. Other treatment sites may include areas or regions of the body including any hollow anatomical structures.

The foregoing description is provided to enable a person skilled in the art to practice the various configurations described herein. While the subject technology has been particularly described with reference to the various Figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. An implant for occluding an aneurysm, comprising:
a dual-layer braided body having distal and proximal portions, and the braided body formed of a tubular member having first and second longitudinal sections, wherein the first longitudinal section is everted over the second longitudinal section to form the dual-layer braided body, the first and second longitudinal sections having respective first and second porosities, wherein the first and second porosities are different, the distal portion of the dual-layered braided body comprising a closed-end and having a fold whereby the first and second longitudinal sections are coupled at and extend from the fold, the first and second longitudinal sections overlapping each other to cumulatively provide a third porosity at the distal portion and a fourth porosity at the proximal portion, the third and fourth porosities being less than the first and second porosities.

2. The implant of claim 1, wherein the fourth porosity is less than the third porosity.

3. The implant of claim 1, wherein the third porosity is less than the fourth porosity.

4. The implant of claim 1, wherein the fourth porosity is constant from the proximal portion across a midsection of the body.

5. The implant of claim 1, wherein the second porosity is less than the first porosity.

6. The implant of claim 1, wherein the first porosity is substantially constant along the first longitudinal section.

7. The implant of claim 1, wherein the first porosity increases along the length of the first longitudinal section from the distal portion to the proximal portion of the dual-layered braided body.

8. The implant of claim 1, wherein the second porosity is substantially constant along the second longitudinal section.

9. The implant of claim 1, wherein the second porosity decreases along the length of the first longitudinal section from the distal portion to the proximal portion of the dual-layered braided body.

10. The implant of claim 1, wherein the proximal portion is substantially flat.

* * * * *